United States Patent
Marc

(10) Patent No.: US 10,290,201 B2
(45) Date of Patent: May 14, 2019

(54) GLUCOSE METER WITH ALARM

(71) Applicant: Linda Marc, Milton, MA (US)

(72) Inventor: Linda Marc, Milton, MA (US)

(*) Notice: Subject to any disclaimer, the term of this patent is extended or adjusted under 35 U.S.C. 154(b) by 0 days.

(21) Appl. No.: 15/394,403

(22) Filed: Dec. 29, 2016

(65) Prior Publication Data

US 2017/0186305 A1    Jun. 29, 2017

Related U.S. Application Data

(60) Provisional application No. 62/272,645, filed on Dec. 29, 2015.

(51) Int. Cl.
| | | |
|---|---|---|
| *A61B 5/00* | (2006.01) | |
| *A61B 5/145* | (2006.01) | |
| *G01N 33/49* | (2006.01) | |
| *G06F 19/00* | (2018.01) | |
| *G08B 21/24* | (2006.01) | |
| *G16H 40/67* | (2018.01) | |

(52) U.S. Cl.
CPC ............ *G08B 21/24* (2013.01); *A61B 5/0022* (2013.01); *A61B 5/14532* (2013.01); *A61B 5/4848* (2013.01); *A61B 5/742* (2013.01); *A61B 5/7405* (2013.01); *A61B 5/746* (2013.01); *A61B 5/7455* (2013.01); *G01N 33/49* (2013.01); *G06F 19/00* (2013.01); *G16H 40/67* (2018.01); *A61B 5/486* (2013.01)

(58) Field of Classification Search
CPC .................. A61B 5/14532; G06F 19/3406
See application file for complete search history.

(56) References Cited

U.S. PATENT DOCUMENTS

| | | | |
|---|---|---|---|
| 2003/0211617 A1* | 11/2003 | Jones | A61B 5/14532 436/14 |
| 2008/0119702 A1 | 5/2008 | Reggiardo | |
| 2009/0156923 A1* | 6/2009 | Power | A61B 5/14532 600/365 |
| 2011/0034909 A1* | 2/2011 | Lebel | A61M 5/14276 604/891.1 |
| 2013/0012796 A1 | 1/2013 | Kak et al. | |
| 2013/0030841 A1* | 1/2013 | Bergstrom | A61B 5/0002 705/3 |
| 2014/0012510 A1 | 1/2014 | Mensinger et al. | |
| 2014/0066735 A1* | 3/2014 | Engelhardt | A61B 5/14532 600/365 |
| 2015/0242585 A1* | 8/2015 | Spiegel | G06F 19/3418 705/2 |

* cited by examiner

*Primary Examiner* — Fabricio R Murillo Garcia
(74) *Attorney, Agent, or Firm* — Argus Intellectual Enterprise; Daniel Enea; Jordan Sworen

(57) ABSTRACT

A glucose meter with an adjustable alarm and an integral wireless transmitter to send a user a reminder to take a second glucose level measurement. The glucose meter with an alarm features a housing with a display and input buttons connected to a microprocessor. The housing has a slot designed to accept a strip with a sample of blood. A glucose level sensor within the housing is adapted to measure the glucose level of the blood sample. After the measurement is taken, an alarm is set to activate after a predetermined period of the time, reminding a user to take a second glucose level measurement. The alarm can be an auditory or a vibrating alarm. Additionally, the wireless transmitter is designed to send an email or text message to a user as a reminder to take a second glucose level measurement.

14 Claims, 2 Drawing Sheets

GLUCOSE METER WITH ALARM

CROSS REFERENCE TO RELATED APPLICATIONS

This application claims the benefit of U.S. Provisional Application No. 62/272,645 filed on Dec. 29, 2015. The above identified patent application is herein incorporated by reference in its entirety to provide continuity of disclosure.

BACKGROUND OF THE INVENTION

The present invention relates to blood glucose level meters. More specifically, the present invention relates to a blood glucose meter with an integral wireless transmitter and an adjustable alarm that can be programed to be activated after a specific predetermined interval of time has passed in order to remind a user to take a second glucose level measurement. The wireless transmitter is connected to a microprocessor and designed to send an email or text message to a user as a reminder to take the second glucose level measurement.

Diabetic individuals are required to keep their glucose blood levels within an acceptable range. Food, and specifically carbohydrates, raises blood glucose levels while insulin reduces them. In order to ensure that their blood glucose levels are consistently kept within the safe range, a user must balance their food intake with insulin medication. In order to properly accomplish this, an accurate reading of the blood glucose levels of a diabetic individual at various points throughout the day is vital. Specifically, a measurement of blood glucose levels is often required to be taken prior to a meal and again post-meal after a specific interval of time has elapsed. The timing of these measurements is crucial to recording accurate and useful data.

Glucose meters that are configured to measure the current glucose levels of an individual from a sample of blood are known. Many traditional glucose meters lack an adjustable alarm function. The meal schedule of an individual can often vary vastly from day to day. Even those who strive to be meticulous about recording their glucose levels may find that an occasional unexpected event may arise that will delay their ability to take a blood glucose level reading. Accordingly, a glucose meter than can have an adjustable alarm set incorporate an individual's changing meal schedule is desired.

SUMMARY OF THE INVENTION

In view of the foregoing disadvantages inherent in the known types of blood glucose meters now present in the known art, the present invention provides a blood glucose meter with an alarm wherein the same can be utilized for providing convenience for the user by providing an adjustable alarm. The present system comprises a housing having a display and input buttons placed thereon and operably connected to a microprocessor. A slot is disposed on the housing and configured to accept a strip with a blood sample. A glucose level sensor is positioned next to the slot within the housing and is adapted to measure the glucose level of the blood sample. After the blood glucose measurement is taken, an alarm is configured to activate after a predetermined period of the time has elapsed, reminding a user to take a second blood glucose measurement. The alarm can be an auditory or vibrating alarm. Additionally, a wireless transmitter is connected to the microprocessor and designed to send an email or text message to a user as a reminder to take a second glucose level measurement.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
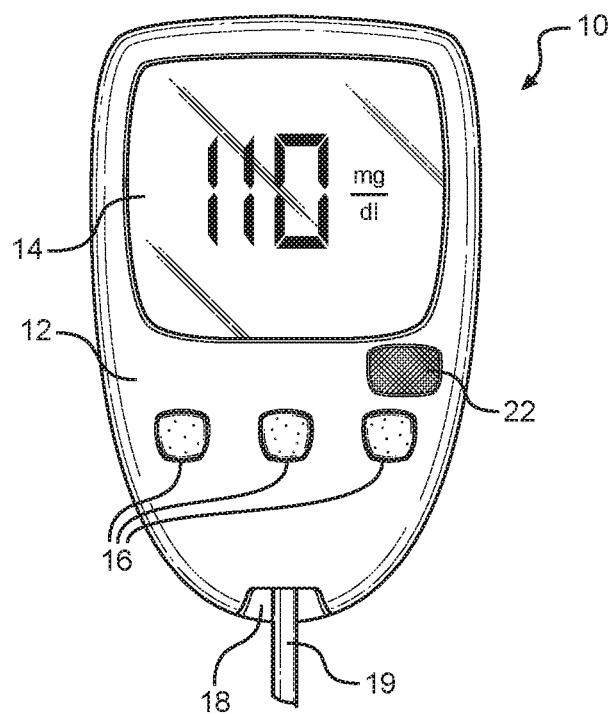
FIG. 1 shows a front view of one embodiment of the glucose meter with an alarm.

Reference is made herein to the attached drawings. Like reference numerals are used throughout the drawings to depict like or similar elements of the glucose meter with alarm. The figures are intended for representative purposes only and should not be considered to be limiting in any respect.

Figure 2:
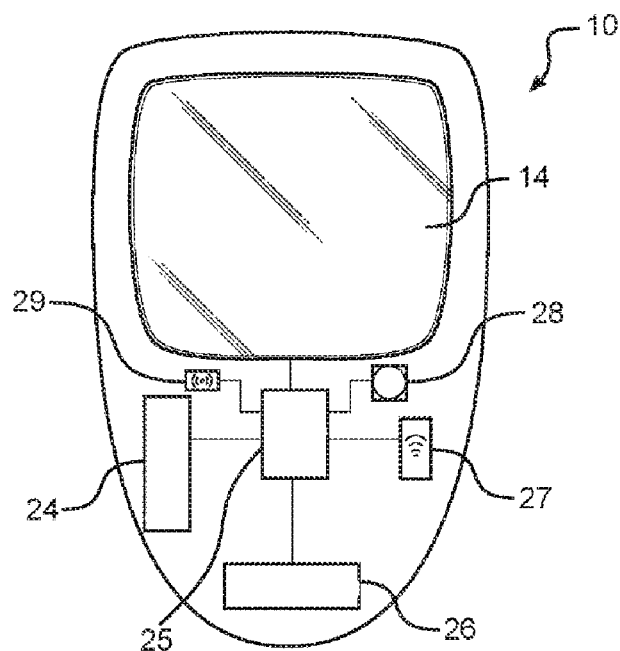
FIG. 2 shows a schematic view of the glucose meter with an alarm.

Referring now to FIGS. 1 and 2, there is shown a front view and a schematic view of the glucose meter with an alarm. The glucose meter with an alarm 10 comprises a housing 12 forming an interior volume and having a display screen 14 disposed on a front side thereof. The display screen 14 is configured to indicate the measured blood glucose level from a sample of blood. A plurality of buttons 16 is positioned on the front side of the housing 12 and an input port 18 is placed at an edge of the housing 12. In some embodiments of the glucose meter with an alarm 10, the input port 18 is positioned on a perimeter edge of the housing 12, at an end of the housing opposing the display screen 14, as seen in FIG. 1. The slot of the input port 18 is adapted to receive an elongated test strip 19 containing a sample of an individual's blood thereon.

A microprocessor 25 is disposed within the interior volume. The microprocessor 25 is operably connected to a computer readable memory 24, such as random access memory, a blood glucose level sensor 26, and a wireless transmitter 27. Additionally, the microprocessor 25 is connected to an alarm. In some embodiments of the glucose meter with an alarm 10, the alarm is an auditory speaker 28. In further embodiments, the alarm comprises a vibrating motor 29 configured to vibrate or shake when the alarm is activated.

In order to ensure a meaningful and accurate blood glucose level is recorded, diabetic patients are often required to take a first measurement prior to eating a meal and a second, post meal, measurement after a specific interval of time has elapsed. For many diabetic patients, two hours after eating a meal is the time at which their glucose levels reach a peak value. If the second measurement is taken closer to the meal or after the two hour mark, the glucose levels recorded are likely to be lower that the peak value, and a patient is thus unable to properly gauge their blood glucose levels.

In use, an individual takes a first measurement before a meal which in a low-glucose state. The user draws a small amount of blood and places it on a test strip. The test strip 19 is then inserted into the input port 18 of the glucose meter with alarm 10. The blood glucose sensor 26 detects the amount of glucose within the blood sample. The microprocessor 25 is configured to then save testing data, which includes the recorded glucose level, to the computer readable memory 24 for future reference. In some embodiments, the testing data further includes the time of measurement as well. The plurality of buttons 16 are used to set an alarm as a reminder for a user to take a second blood glucose measurement after a predetermined period of time as passed. This period can vary according to the needs of the user. As previously mention, this time period is often 2 hours. After the time period has elapsed, the alarm is activated to remind a user to take the second measurement of blood glucose levels. For example, an auditory or a vibrating alarm is triggered. In some embodiments both an auditory and vibrating alarm is activated simultaneously. A user may recall and review the prior recorded blood glucose levels that have been recorded in the computer readable memory at a later date for reference.

In some embodiments of the glucose meter with alarm 10, the alarm is automatically set to run the predetermined period of time, for example two hours, once a first glucose level has been measured. In alternative embodiments, the alarm is set when the user activates it via the plurality of buttons 16. Thus, a able to easily set the time when the alarm of the glucose meter with alarm 10 in accordance with their schedule.

In further embodiments of the glucose meter with an alarm, a message is sent via the wireless transmitter 27 to a remote receiver when the alarm is activated. In some embodiments, the remote receiver s a mobile device, such as a cellular phone or tablet computer. The message be may be transmitted using a Bluetooth or similar short distance communication protocol, wherein the glucose meter is paired with a user's mobile phone. Alternatively, a message may be sent over a wireless network. The message may be a text or email message. This allows the glucose meter with an alarm 10 to send a reminder to a user even if they are carrying their mobile phone but not the glucose meter at the time.

Figure 3:
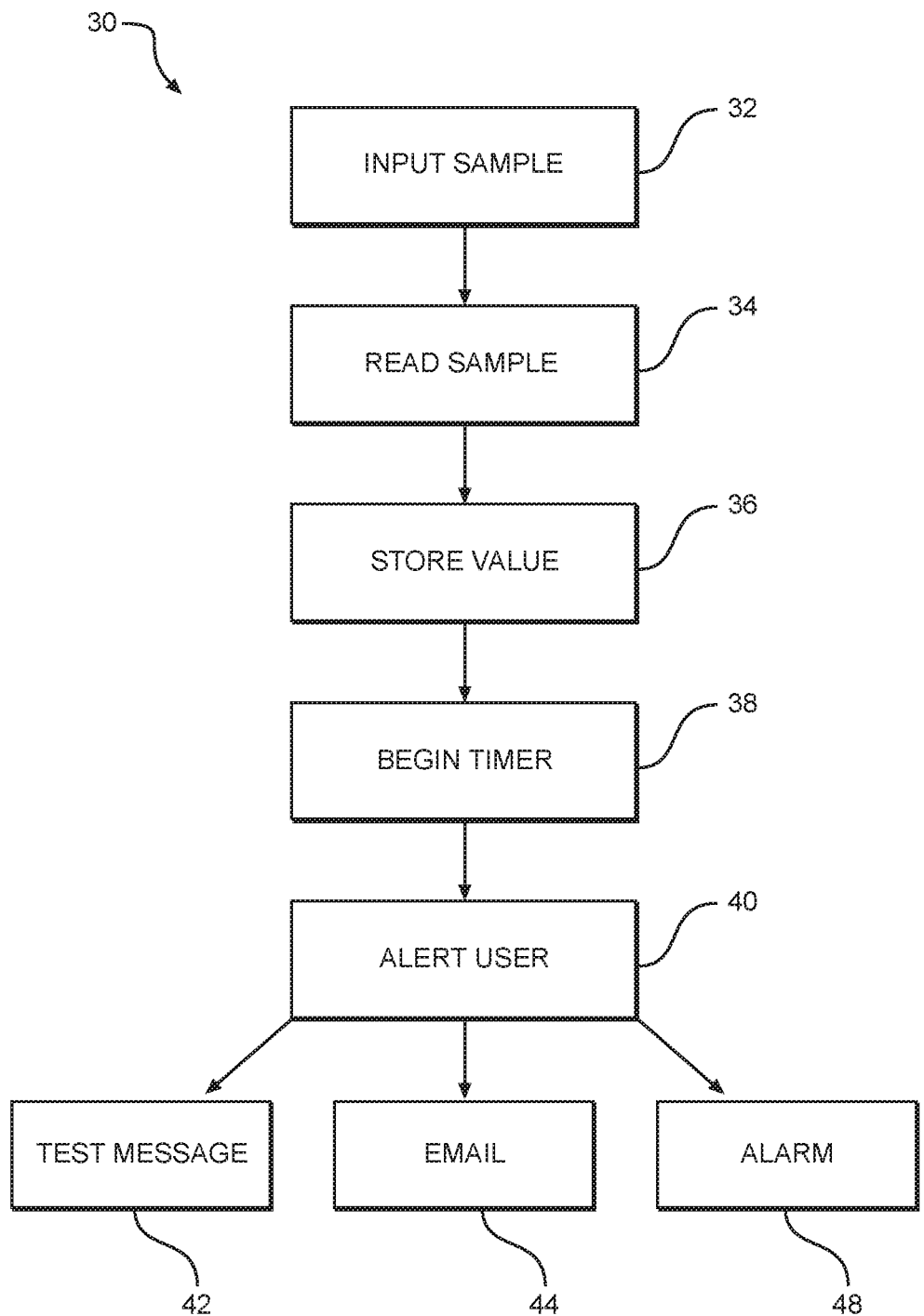
FIG. 3 shows a flow chart of the method of setting an alarm for a blood glucose test.

Referring now to FIG. 3, there is shown a flow chart of the method of setting an alarm for a blood glucose meter. The method 30 comprises receiving a test strip containing a blood sample into an input port of a glucose meter 32, detecting the glucose level from the blood sample 34, recording and storing the glucose level 36 for future reference, displaying the recorded glucose level on a display screen, setting a timer to activate an alarm 38 after a predetermined period of time has elapsed, and activating the alarm after the passage of such period of time 40. The alarm may be via an auditory or mechanical alarm 48, such as a vibrating alarm, or a message sent via a wireless network, such as an email 44 or a text message 42.

According to some embodiments, the operations, techniques, and/or components described herein can be implemented as (i) a special-purpose computing device having specialized hardware and a logic hardwired into the computing device to persistently perform the disclosed operations and/or techniques or (ii) a logic that is implementable on an electronic device having a general purpose hardware processor to execute the logic and a computer-readable medium, e.g. a memory, wherein implementation of the logic by the processor on the electronic device provides the electronic device with the function of a special-purpose computing device.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A glucose meter, comprising:
a housing including;
an input slot configured to receive a test strip, wherein a glucose sensor detects a glucose level of blood from the test strip when inserted therein;
the glucose meter configured to set a post-meal blood glucose alarm to test a post-meal blood glucose level, the post-meal blood glucose alarm configured to activate after a period of time based on an immediately preceding pre-meal blood glucose level;
a computer readable memory configured to store testing data;
wherein the testing data includes the post-meal blood glucose level and the pre-meal blood glucose level;
a display screen configured to display the testing data;
a secondary alarm programmable via a plurality of buttons, the plurality of buttons disposed on the housing;
wherein the period of time increases in duration upon a detection of a higher than predetermined blood glucose level;
wherein a wireless transmitter is configured to communicate a message to a remote receiver when either the post-meal blood glucose alarm or the secondary alarm is activated.

2. The glucose meter of claim 1, further comprising a vibrating motor configured to vibrate when the post-meal blood glucose alarm or the secondary alarm is activated.

3. The glucose meter of claim 1, further comprising an auditory alarm configured to sound when the post-meal blood glucose alarm or the secondary alarm is activated.

4. The glucose meter of claim 1, wherein the remote receiver is a mobile device, such as a cellular phone or a tablet computer.

5. The glucose meter of claim 1, wherein the message is sent to the remote receiver over a short distance communication protocol.

6. The glucose meter of claim 5, wherein the short distance communication protocol is a Bluetooth protocol.

7. The glucose meter of claim 1, wherein the message is a digital text message sent over a wireless network.

8. The glucose meter of claim 1, wherein the message is an email message sent over a wireless network.

9. A method of setting an alarm for a blood glucose meter, comprising:
receiving a test strip in an input port;
detecting a glucose level of a blood sample from the test strip via a glucose sensor;

setting a post-meal blood glucose alarm to test a post-meal blood glucose level, the post-meal blood glucose alarm configured to activate after a period of time based on an immediately preceding pre-meal blood glucose level;

adjusting the period of time increases in duration upon a detection of a higher than a predetermined blood glucose level;

recording testing data on a computer readable medium, wherein the testing data comprises the post-meal blood glucose level and the pre-meal blood glucose level;

displaying the testing data on a display screen;

activating the post-meal blood glucose alarm after the period of time has elapsed.

10. The method of claim 9, wherein the post-meal blood glucose alarm is an auditory alarm.

11. The method of claim 9, wherein the post-meal blood glucose alarm is a vibrating alarm.

12. The method of claim 9, wherein the post-meal blood glucose alarm is a message sent to a remote receiver.

13. The method of claim 12, wherein the message is in the form of a text message sent over a wireless network.

14. The method of claim 12, wherein the message is in the form of an email message sent over a wireless network.

\* \* \* \* \*